United States Patent [19]

Winkler

[11] 4,293,522

[45] Oct. 6, 1981

[54] ELECTROPHOTOLYSIS OXIDATION SYSTEM FOR MEASUREMENT OF ORGANIC CONCENTRATION IN WATER

[75] Inventor: H. Eugene Winkler, Friendswood, Tex.

[73] Assignee: The United States of America as represented by the Administrator of the National Aeronautics and Space Administration, Washington, D.C.

[21] Appl. No.: 41,145

[22] Filed: May 21, 1979

[51] Int. Cl.³ ............................................. G01N 31/12
[52] U.S. Cl. ................................. 422/80; 23/230 PC; 23/232 E; 204/1 T; 204/195 S; 204/263; 204/264; 204/266; 204/275; 204/276; 204/278
[58] Field of Search ...................... 23/230 PC, 232 E; 422/78–80; 204/257, 258, 263–266, 275–278, 195 S, 1 K, 103

[56] References Cited

U.S. PATENT DOCUMENTS

| | | | |
|---|---|---|---|
| 3,224,837 | 12/1965 | Motat | 23/230 PC |
| 3,345,274 | 10/1967 | Schmidt | 204/38 A |
| 3,607,071 | 9/1971 | Staffin et al. | 422/79 |
| 3,788,965 | 1/1974 | Holsinger | 204/261 |
| 3,854,877 | 12/1974 | Csaky et al. | 422/79 |
| 3,955,935 | 5/1976 | Northmore et al. | 422/78 |
| 3,958,941 | 5/1976 | Regan | 422/80 |
| 3,964,868 | 6/1976 | DiCola et al. | 422/62 |
| 4,039,409 | 8/1977 | LaConti et al. | 204/129 |
| 4,056,452 | 11/1977 | Campbell | 204/258 |
| 4,057,479 | 11/1977 | Campbell | 204/258 |

Primary Examiner—G. L. Kaplan
Attorney, Agent, or Firm—Edward K. Fein; John R. Manning; Marvin F. Matthews

[57] ABSTRACT

Methods, and apparatus for use therein, for determining organic carbon in aqueous solution which method comprises subjecting the aqueous solution to electrolysis, for generating oxygen from water, and simultaneously to ultraviolet radiation, for oxidation of substantially all organic carbon therein to carbon dioxide and subsequently measuring said carbon dioxide and relating the value to the concentration of organic carbon in said aqueous solution.

7 Claims, 5 Drawing Figures under within which the process of the present invention may be performed.

ELECTROPHOTOLYSIS OXIDATION SYSTEM FOR MEASUREMENT OF ORGANIC CONCENTRATION IN WATER

ORIGIN OF THE INVENTION

The invention described herein was made by an employee of the United States Government and may be manufactured and used by or for the Government of the United States of America for governmental purposes without the payment of any royalties thereon or therefor.

BACKGROUND OF THE INVENTION

1. Field of the Invention

The present invention relates to an improved method for the determination of total organic carbon in aqueous solutions, and to apparatus useful for performance of said method. Particularly, the method of the present invention relates to oxidizing organic carbon present in aqueous solution to carbon dioxide, with subsequent detection of carbon dioxide for determination of total organic carbon originally present in said aqueous solution. The apparatus of the present invention comprises a cell within which the organic carbon species are oxidized, and related to detection apparatus.

2. Description of the Prior Art

The determination of organic carbon in aqueous solution is commonly performed for such purposes as controlling the amount of organic compounds present in recycle streams, and monitoring organic compound content of waste streams. Methods, and apparatus useful therein, for such organic carbon determination are well known in the art. For example, See U.S. Pat. No. 3,854,877, Casky et al; U.S. Pat. No. 3,964,868, DiCola et al; U.S. Pat. No. 3,955,924, Northmore et al; U.S. Pat. No. 3,958,941, Regan et al; and U.S. Pat. No. 3,607,071, Staffin et al.

U.S. Pat. No. 3,958,941 discloses a process, and equipment therefor, for determining organic carbon in aqueous mixture, wherein an organic sample introduced into a water stream circulating through a reaction cell is oxidized with air in the presence of an ultraviolet light source to form carbon dioxide. Such carbon dioxide, stripped from said circulating water stream, is dissolved in a second stream of water in a measuring chamber. Resistivity of water in the measuring chamber is measured, and this measurement is related to the amount of carbon originally introduced into said oxidation chamber. This process requires air as a source of oxygen for oxidizing carbon present and stripping carbon dioxide from water present in the oxidation chamber. Additionally, this process requires substantial equipment and piping for circulating and recycling the various gas and liquid streams employed.

U.S. Pat. No. 3,224,837, Peter Moyat, discloses a process for determining organic carbon in water which comprises adjusting pH of an organic containing water sample to the acid range, subjecting said pH adjusted water sample to electrolysis for production of oxygen, oxidizing, with said oxygen, organic carbon present to $CO_2$, and measuring carbon dioxide content of the gas evolved from such electrolysis step for determining the organic carbon originally present in said water sample. This process requires an acid pH for said water sample to aid electrolysis of water to oxygen and hydrogen, and for releasing carbon dioxide formed by oxidation from solution in said water sample. Consequently, acid for adjusting the water sample pH must be provided, and after determination of the organic carbon content, the acidic water sample must generally be discarded. Further, the electrolysis process of Moyat is not effective for oxidizing refractory organic compounds such as ethanol, acetic acid, amino acids, and fats. Consequently, Moyat provides a catalytic oxidation stage for completing oxidation of such refractory organic compounds in the vapor phase.

SUMMARY OF THE INVENTION

Now according to the present invention I have discovered an improved method for oxidizing organic compounds in aqueous solution into carbon dioxide. Further, I have discovered a novel system, within which said improved method may be practiced, useful in determination of organic carbon content of an aqueous solution.

In one embodiment, the method of the present invention comprises contacting an organic carbon containing aqueous solution with the anode of an electrolysis cell comprising an anode and cathode separated by a solid polymeric electrolyte wherein said cathode is maintained remote from said aqueous solution; supplying sufficient direct current electric power to said electrolysis cell for electrolysis of water in said aqueous solution into oxygen at said anode and hydrogen at said cathode; simultaneous with electrolysis of said water, irradiating said aqueous solution with ultraviolet radiation for reaction of substantially all organic carbon present with said oxygen to form carbon dioxide dissolved in said aqueous solution, and, upon substantially complete oxidation of said organic carbon, detecting the amount of carbon dioxide in said aqueous solution for determination of the amount of organic carbon originally present.

Apparatus of the present invention comprises an oxidation cell, including said electrolysis cell and an ultraviolet light source, within which oxidation of organic carbon is accomplished; and comprises associated equipment for transporting said aqueous solution, and for determining carbon dioxide content thereof.

Advantages of the present invention include generation of oxygen in situ, thus dispensing with air or other source of oxygen; the electrolysis of water may be accomplished without addition of acid electrolyte to the aqueous solution; aqueous solution, after determination of carbon dioxide content, may be returned to its source and need not be separately disposed of; and the process, employing apparatus of the present invention, may be operated continuously. These and other advantages will be discussed in more detail below.

DETAILED DESCRIPTION OF THE INVENTION

In many processes, such as: sewage treating; food processing; chemical manufacture; etc., as well as in processes for recycling water from human body wastes for subsequent human consumption (as in a space vehicle), aqueous streams containing relatively small amounts of organic compounds in solution are generated. For a variety of reasons such as pollution control, human health, process control, etc., it is desirable to monitor the organic content of said aqueous streams, such that appropriate control measures may be undertaken.

Determination of organic carbon content of such aqueous streams is commonly made by oxidizing, with oxygen, such organic carbon to carbon dioxide; detection of the amount of such carbon dioxide, either in solution or as a gas stripped from said aqueous solution; and subsequently determining organic carbon content of said aqueous solution from the detected amount of carbon dioxide. The present invention is an improved process, and apparatus for use therein, for such determination of organic carbon content of an aqueous solution.

Figure 1:
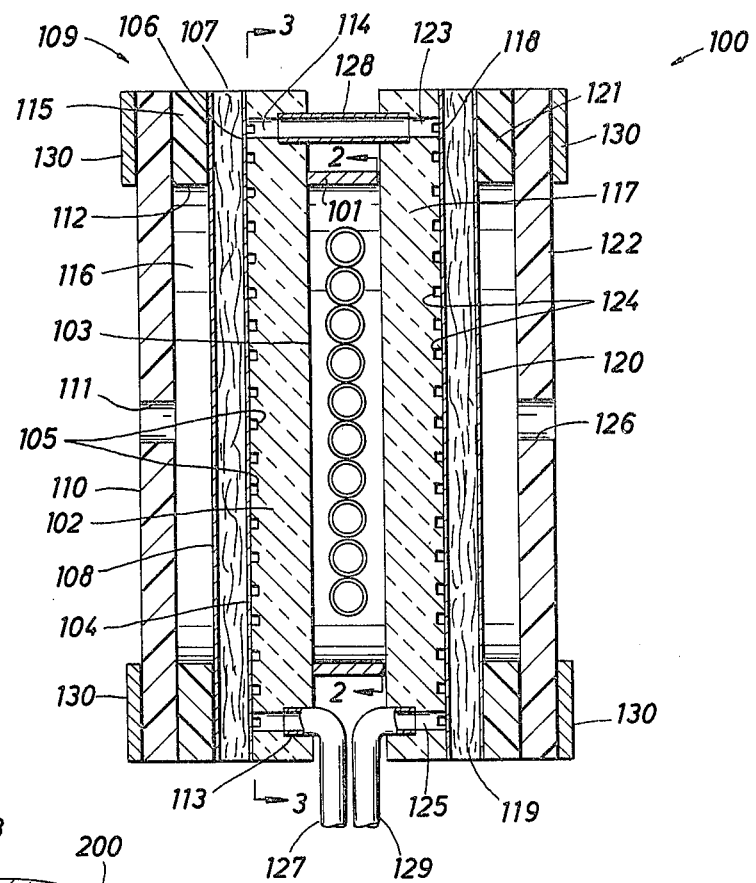
FIG. 1 is a representation of an oxidation cell embodying improvements of the present invention.

The present invention may be better understood by reference to the drawings. In FIG. 1, said oxidation cell 100 comprises a source of ultraviolet radiation 101. Adjacent said source 101 is first transparent quartz plate 102, having a first face 103 and a second face 104 defining a labyrinthine flow channel 105.

Aqueous solution inlet opening 113 and aqueous solution outlet opening 114 pass through said first quartz plate 102 from the two ends of said flow channel 105 to said first face 103. A water pervious anode 106 is in electrical contact with said first quartz plate second face 104 for containing an aqueous solution within said flow channel 105. Said anode 106 is in electrical contact with the positive pole of a direct electric current source, not shown.

The side of said anode 106 remote from said first quartz plate 102 is in electrical contact with a solid, water insoluble electrolyte plate 107. The side of said electrolyte plate 107 remote from said anode plate 106 is in electrical contact with a gas pervious cathode plate 108. Said cathode plate 108 is in electrical contact with the negative pole of said direct electrical current source, not shown. Contacting said cathode plate 108 on the side remote from said electrolyte plate 107, is hydrogen collection plate 109 comprising a gas-tight outer ring 115 and a gas pervious center portion 116. Said cathode plate 108 and said collection plate ring 115 are in gas-tight contact, such that hydrogen generated at said cathode plate 108 enters said collection plate center portion 116. A gas-tight cover plate 110, having a hydrogen outlet opening 111, covers said hydrogen collection ring 109.

In FIG. 1, on the side of ultraviolet radiation source 101 opposite said quartz plate 102, is an array of second quartz plate 117; second annode plate 118, second solid, water insoluble electrolyte plate 119; second cathode plate 120, second hydrogen collection plate 121, and second cover plate 122, all in association and connected in the same manner as their counterparts on the opposite side of said ultraviolet radiation source 101. Second quartz plate 117 has aqueous solution inlet opening 123, flow channel 124 and aqueous solution outlet opening 125. Cover plate 122 has hydrogen outlet opening 126. Further description of these second elements is unnecessary as such description would merely duplicate the description of the corresponding elements previously described.

In FIG. 1, aqueous solution charge conduit 127 is in open communication with quartz plate inlet opening 113. Aqueous solution transfer conduit 128 connects with, and provides communication between quartz plate outlet opening 114 and second quartz plate inlet opening 123. Aqueous solution outlet conduit 129 is in open communication with second quartz plate outlet opening 125. Elements of said oxidation cell are held in association by clamping means 130.

Figure 2:
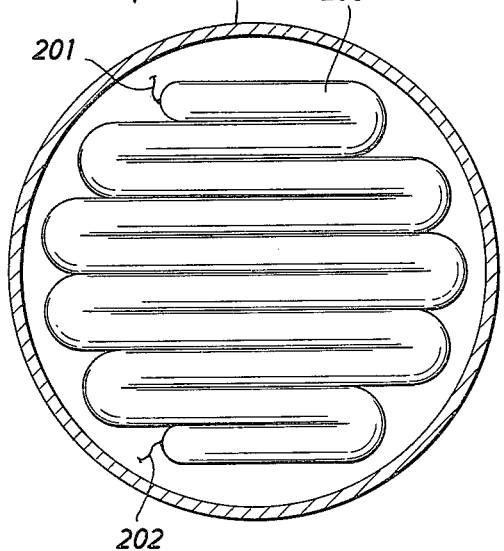
FIG. 2 is Section 2—2 of FIG. 1, showing an ultraviolet radiation means.

In FIG. 2, one embodiment of ultraviolet radiation source 101 is shown in plane view, which corresponds to section 2—2 of FIG. 1. Said ultraviolet radiation source comprises a transparent gas discharge tube 200 having electrical connections 201 and 202 for connection to an appropriate electrical power supply, not shown. Said gas discharge tube may be any known radiator of ultraviolet radiation, such as a mercury vapor discharge tube. Said gas discharge tube 200 is contained within retaining member 203, a cylindrical ring which protects said discharge tube 200 from injury.

Figure 3:
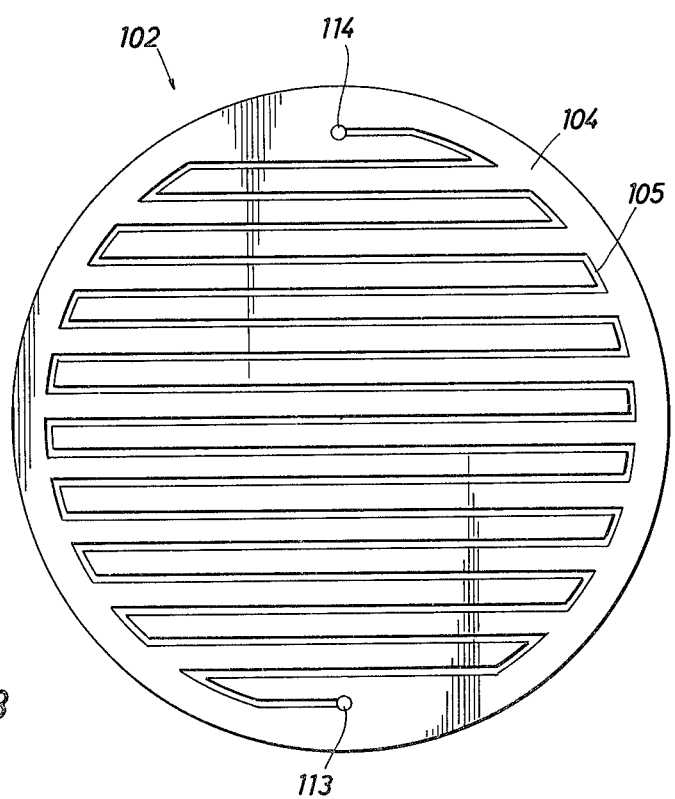
FIG. 3 is Section 3—3 of FIG. 1, showing a plane view of a quartz plate with a flow channel therein.

In FIG. 3, quartz plate 102 is shown in plane view with quartz plate second face 104 uppermost, which corresponds with section 3—3 of FIG. 1. This view of quartz plate 107 is also typical for second quartz plate 117.

In FIG. 3 quartz plate inlet opening 113 connects with one end of flow channel 105, and quartz plate outlet opening 114 connects with the other end of flow channel 105.

In operation of the oxidation cell 100, ultraviolet radiation source 101 is energized such that ultraviolet radiation passes through transparent quartz plates 102 and 117 and irradiates flow channels 105 and 124. Direct current electric power, of preferably about 2–4 volts potential, is applied to said anode plates 106 and 118 and to said cathode plates 108 and 120 at a current density sufficient for electrolysis of water to form hydrogen at said cathodes 108 and 120 and oxygen at said anodes 106 and 118. An aqueous solution containing organic carbon flows through inlet conduit 127 into flow channel 105 from whence it flows via outlet 114, transfer conduit 128, inlet 123 into second flow channel 124. From second flow channel 124, said aqueous solution flows via outlet 125 into outlet conduit 129. In flow channel 105 and second flow channel 124, said aqueous solution is irradiated with ultraviolet radiation. A portion of the water in said aqueous solution in contact with anodes 106 and 118 also contacts electrolyte plates 107 and 119, whereupon, under influence of the applied direct electric current, said water is electrolyzed to hydrogen and oxygen. Hydrogen gas generated at cathodes 108 and 120 is collected in hydrogen collection plates 109 and 121 and is vented via hydrogen outlet openings 111 and 126.

Oxygen generated at said anode plates 106 and 118 passes into said aqueous solution wherein, catalyzed by said ultraviolet radiation, it reacts with organic carbon present to form carbon dioxide. By properly adjusting direct current density for controlling the rate of oxygen formation, and adjusting the rate of aqueous solution flow, essentially all organic carbon present may be oxidized to carbon dioxide within said oxidation cell 100.

Aqueous solution containing carbon dioxide flow from oxidation cell 100 via line 129 to carbon dioxide detectors, or further processing, not shown. In one embodiment, pressure upon said aqueous solution is maintained sufficiently high such that substantially all carbon dioxide remains in solution.

Figure 4:
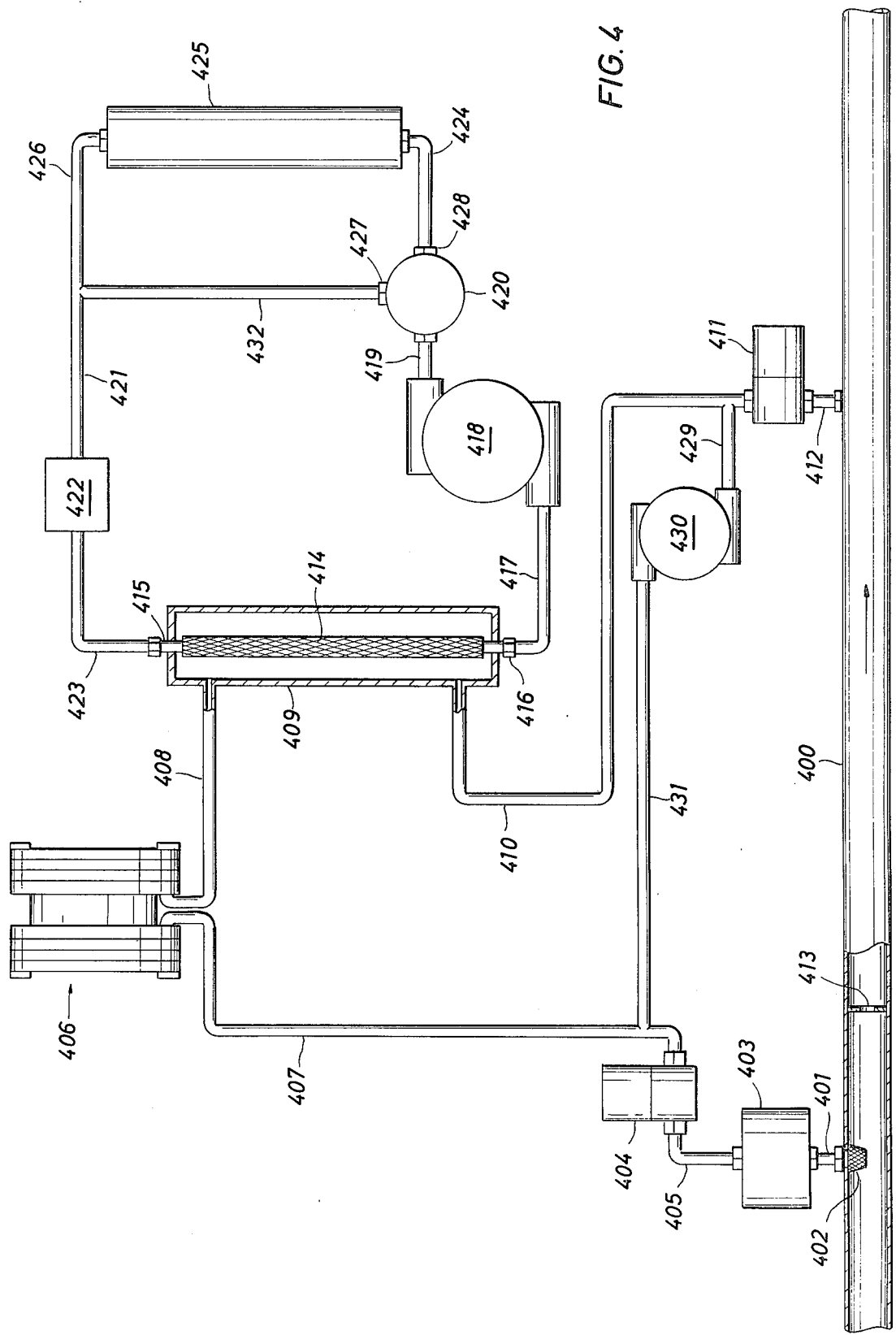
FIG. 4 is a schematic representation of a first system within which the process of the present invention may be performed, said system employing absorption of carbon dioxide from said aqueous solution into an amount of deionized water, and subsequent determination of carbon dioxide content of said water.

In FIG. 4, one embodiment of the present invention, comprising a system for determining total organic carbon in an aqueous solution is disclosed. Said system comprises, in combination, a water conduit 400, having a water outlet nipple 401. Interior to water conduit 400 and in association with outlet nipple 401 is debris trap 402. The inlet of a particulate filter 403 is in communication with nipple 401 at the end opposite water conduit 400. The outlet of particulate filter 403 is in open communication with the inlet solenoid valve 404 via conduit 405. The outlet of solenoid valve 404 is in open communication with the inlet of oxidation cell 406 via conduit 407. In a preferred embodiment, oxidation cell 406 is an oxidation cell as shown in FIG. 1 herein. The outlet of oxidation cell 406 is in open communication, via conduit 408 with one end of elongated vessel 409. The other end of said vessel 409 is in open communication via line 410 with the inlet of solenoid valve 411. The outlet of solenoid valve 411 is in open communication, via conduit 412 with the interior of water conduit 400 at a point downstream from nipple 401. A flow restriction 413 is located interior of said water conduit 400 at a point between nipple 401 and conduit 412.

In FIG. 4, conduit 410 is in open communication, via conduit 429 with the inlet of pump 430. The discharge of pump 430 is in open communication, via conduit 431 and conduit 407 with oxidation cell 406. An elongated hollow fiber membrane 414, pervious to carbon dioxide but impervious to water, and having an inlet nipple 415 and an outlet nipple 416, is located within vessel 409 such that inlet nipple 415 and outlet nipple 416 extend through opposite ends of vessel 409, and the membrane 414 is totally enclosed within vessel 409. Vessel 409 has openings at the ends through which inlet nipple 415 and outlet nipple 416 may extend. A water and gas impervious seal (not shown) is maintained between the openings in vessel 409 and inlet nipple 415 and outlet nipple 416.

In FIG. 4, membrane outlet nipple 416 is in open communication, via conduit 417 with the inlet of circulation pump 418. The discharge of circulation pump 418 is in open communication via conduit 419 with the inlet of 3-way valve 420, having a first outlet 427 and a second outlet 428. First valve outlet 427 is in open communication via conduit 432 and 421 with conductivity sensor 422. Conductivity sensor 422 measures electrical conductivity of a fluid and produces an electrical signal proportional to said fluid conductivity. Such conductivity sensors are articles of commerce and will not be further described herein.

In FIG. 4, second valve outlet 428 is in open communication, via conduit 424 with the inlet of an ion exchange column 425 suitable for removing cations and anions from water solution. The outlet of ion exchange column 425 is in open communication via conduit 426 and 421 with the inlet of conductivity sensor 422. The outlet of conductivity sensor 422 is in open communication, via conduit 423 with the inlet 415 of hollow fibre membrane 414.

In operation, the system of FIG. 4 functions as follows. Solenoid valves 404 and 411 are closed and 3-way valve 420 is positioned such that the inlet and second outlet 428 are open. Oxidation cell 406 is not operated. Water is circulated by pump 418 through ion exchange column 425, conductivity sensor 422 and hollow fibre membrane 414 for a time until the conductivity of said circulated water is reduced, by removal of ions therefrom, to a low value, indicating an ion concentration lower than that which is to be subsequently measured. At this point, 3-way valve 420 is adjusted such that first outlet 427 is open and second outlet 428 is closed such that flow through ion exchange column 425 is prevented and water circulated continues via line 432.

Solenoid valves 404 and 411 are opened such that organic containing aqueous solution flows from line 400 through solenoid valve 404 into oxidation cell 406. Aqueous solution flow continues through conduit 408, vessel 409, and solenoid valve 411. Pressure drop produced by flow restriction 413 forces aqueous solution in this path.

Circulation of aqueous solution through pump 430, oxidation cell 406 and vessel 409 is commenced and solenoid valves 404 and 411 are closed. Circulation of said aqueous solution is continued such that dissolved carbon dioxide, and other transportable ions, equilibrates across said fibre membranes such that carbon dioxide content of the circulating water stream is the same as that of the circulating aqueous solution. A first measurement is then made with said conductivity sensor 422 and the conductivity value obtained is related by mathematical relationships to the carbon dioxide content of said circulating aqueous solution. This first measurement value of carbon dioxide is retained as inorganic carbon concentration in aqueous solution.

Upon obtaining said inorganic carbon concentration, oxidation cell 406 is activated for oxidizing essentially all organic carbon to carbon dioxide. Circulation of aqueous solution is maintained until essentially all organic carbon is oxidized to carbon dioxide, and until said carbon dioxide equilibrates through said fibre membrane between said circulating aqueous solution and said circulating water. Upon carbon dioxide equilibration, a second conductivity measurement of said circulating water stream is made. This second conductivity measurement is converted by mathematical relationships into a measure of total carbon in said circulating aqueous solution. Organic carbon in said circulating aqueous solution is obtained by subtracting inorganic carbon (derived from said first conductivity measurement) from total carbon (derived from said second conductivity measurement).

Upon completion of the determination of organic carbon content in said circulating aqueous solution, the above process is begun at its beginning in preparation for determining organic carbon in a new sample of aqueous solution.

Figure 5:
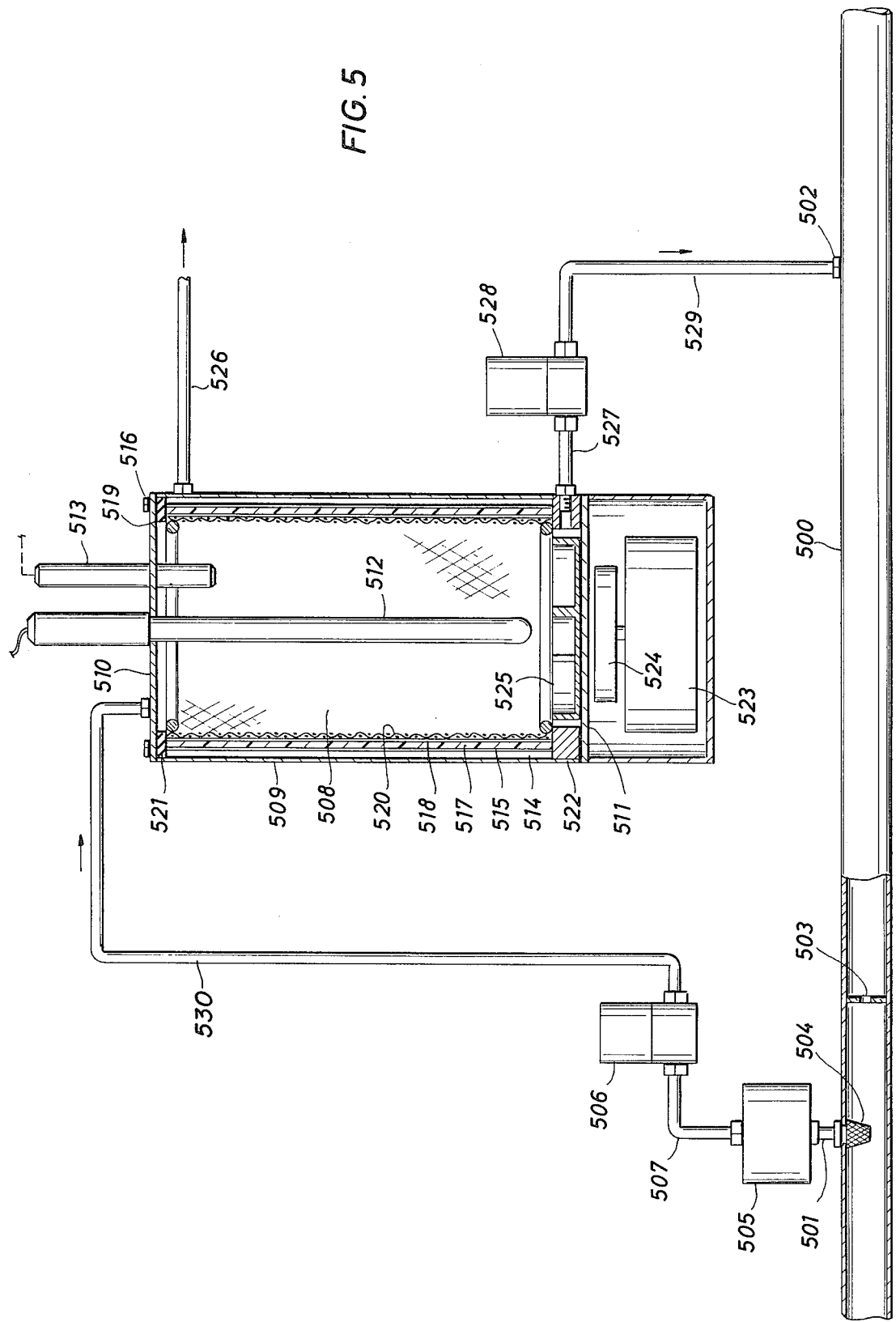
FIG. 5 is a schematic representation of a second system within which the process of the present invention may be performed, said system employing direct measurement of carbon dioxide present in aqueous solution.

In FIG. 5, another embodiment of the present invention, comprising a system for determining organic carbon in an aqueous solution, is disclosed. Said system comprises, in combination, a water conduit 500 having a water outlet nipple 501, a water inlet nipple 502, and an internal restriction 503 located between said nipples 501 and 502. Within said water conduit 500, and in association with inlet nipple 501, is debris trap 504.

In FIG. 5, inlet nipple 501 is in communication with the inlet of a particulate filter 505. The outlet of particulate filter 505 is in open communication with the inlet of a solenoid valve 506 via conduit 507. The outlet of solenoid valve is in open communication with the interior of an oxidation chamber 508 via conduit 530.

In FIG. 5 oxidation chamber 508 operates in the same manner as oxidation chamber 100 shown in FIG. 1, and described hereinabove, however, the configuration is modified to accommodate a stirring mechanism and a carbon dioxide sensor within said chamber, as is completely described herein below. In general, elements of oxidation chamber 100 which were in plate form are configured as open cylinders in oxidation chamber 508.

In FIG. 5, oxidation chamber 508 comprises a cylindrical container 509 having a top 510 and a bottom 511 which is impervious to water and gas and which is non-magnetic. Conduit 530 enters oxidation chamber 508 through an opening provided in top 510. An elongated ultraviolet radiation source 512 such as a Mercury vapor discharge lamp extends into said oxidation chamber 508 via an opening provided in top 510. A carbon dioxide sensor 513, such as a carbon dioxide gas-sensing electrode, extends into said oxidation chamber 508 via an opening provided in top 510.

In FIG. 5, adjacent cylinder 509, and interior to said oxidation chamber 508 is a cylindrical hydrogen collection cavity 514 which is constructed such that hydrogen may freely flow therethrough. Concentric with cylinder 509, and adjacent the interior side of hydrogen chamber 514 is a gas pervious cathode cylinder 515, having an electrical connector 516 extending through top 510 via an opening provided. Concentric with cylinder 509 and in contact with the interior side of cathode 515 is water insoluble solid electrolyte cylinder 517. Concentric with cylinder 509, and in contact with the interior side of electrolyte cylinder 517 is water and gas pervious anode cylinder 518, having an electrical connector 519 extending through top 510 via an opening provided. Concentric with cylinder 509 and adjacent the interior of annode cylinder 518 is a retaining cylinder 520 for maintaining cylinder 515, 517 and 518 positioned within cylinder 509, seal members 521 and 522 are located at the top and bottom of said cylinders to prevent leakage of water into said hydrogen collection cavity.

In FIG. 5, cylinder 509 is mounted above a motor 523 which rotates a magnet 524. In the interior bottom of chamber 508 is a magnetic stirring bar 525 which operates in magnetic interlock with rotating magnet 524 to provide stirring action within said chamber 508.

In FIG. 5, a vent conduit 526 communicates with hydrogen cavity 514 through the wall of cylinder 509 via an opening provided therefor.

In FIG. 5, conduit 527 is in open communication at one end with the interior of chamber 508 via an opening provided in the lower portion of cylinder 509. The other end of conduit 527 is in open communication with the inlet of solenoid valve 528. The outlet of solenoid valve 528 is in open communication with the interior of water conduit 500 via conduit 529 and nipple 502.

In operation of the system of FIG. 5, the process commences operation with valves 506 and 528 open, magnetic stirrer 525 in operation, and with ultraviolet radiation source 512 off and no electric power applied to connectors 516 and 519. Aqueous solution containing organic carbon flows from water conduit 500 through valve 506 and associated conduits into chamber 508, filling it, and continues through valve 528 and associated conduits back into water conduit 500. Such aqueous solution flow is continued until the system is thoroughly flushed, at which time valves 506 and 528 are closed.

Carbon dioxide sensor 513 is activated to obtain a concentration of carbon dioxide in the unoxidized aqueous solution. This value of carbon dioxide is retained as inorganic carbon dioxide. Upon completion of determining inorganic carbon dioxide, the ultraviolet radiation source is activated for irradiating aqueous solution in chamber 508. Electrical power is applied to connectors 519 and 516 to provide sufficient voltage and current density to anode 518 and cathode 515 for electrolysis of a portion of the water present into oxygen at anode 518, and hydrogen at cathode 515. Hydrogen from cathode 515 collects in hydrogen cavity 514 and is vented via conduit 526.

Oxygen from anode 518 enters the aqueous solution in chamber 508 wherein, catalyzed by the ultraviolet radiation present, it oxidizes organic carbon to carbon dioxide. Operation of this system is maintained until substantially all organic carbon is oxidized at, which time the carbon dioxide sensor is activated for determining the carbon dioxide content of the aqueous solution. This carbon dioxide value is retained as total carbon dioxide.

Organic carbon content of the untreated aqueous solution is determined by subtracting inorganic carbon dioxide value from the total carbon dioxide value to obtain a value for carbon dioxide derived from organic carbon, which value is converted by mathematical relationships into a value for organic carbon.

Upon determination of an organic carbon value of said aqueous solution, valves 506 and 528 are opened to admit a new sample of aqueous solution, and the process is repeated.

The process, and apparatus for use therein, described above is particularly useful for determining small concentrations of organic carbon in aqueous solution, e.g. in the range of 0.01 to 100 ppm. Increased operating pressure, which will maintain increased carbon dioxide in aqueous solution may be employed to substantially extend the upper range of organic carbon concentration which may be determined with the above described process and apparatus. Temperatures above ambient are not required for operation of the process herein, as the ultraviolet radiation catalyzes organic carbon oxidation to carbon dioxide. Temperatures in the range of 0°–50° C. are preferred, as below 0° C. the aqueous solution may freeze, and temperatures above 50° C. substantially reduce solubility of carbon dioxide in water. Solid electrolyte employed in the present invention is preferably a polymeric electrolyte membrane, insoluble in water.

In one embodiment, the anode and cathodes are thin metal films attached to said polymeric membrane, as, for example, by vapor deposition, or other effective means. Such polymeric electrolyte films, having cathodic material and annodic materials deposited upon opposite faces thereof are articles of commerce.

It is understood the above-described embodiments of the present invention are illustrative only and that modifications and variations thereof may occur to those skilled in the art. Accordingly, it is intended that the invention herein defined by the appended claims include all such modifications and variations which are within the spirit and scope of said claims, and that no limitation is intended except the limitations of said claims.

I claim:

1. An oxidation cell for oxidizing organic carbon contained in aqueous solution comprising, in combination:

(a) an ultraviolet radiation source in radioactive communication with said aqueous solution;

(b) means for forming a chamber to contain said aqueous solution;

(c) electrolytic cell means adjacent said chamber forming means for electrolyzing water and for forming a barrier to maintain said aqueous solution within said chamber, said electrolytic cell means comprising an anode adjacent said aqueous solution chamber, a solid, water impermeable electrolyte member in electrical contact with said anode and a cathode in electrical contact with said electrolyte member;

(d) hydrogen cavity forming means adjacent said cathode;

(e) means for admitting aqueous solution to said chamber;

(f) means for removing aqueous solution from said chamber; and (g) means for removing hydrogen from the hydrogen cavity.

2. The oxidation cell of claim 1 wherein said ultraviolet radiation source comprises a gas discharge tube configured in a planar array; wherein said chamber forming means comprises a first transparent quartz plate having a first face adjacent a first face of said ultraviolet radiation source and a second face having a first flow channel, said first quartz plate having aqueous solution first inlet means and first outlet means in communication with said flow channel; and wherein said electrolytic cell means comprises a first solid polymeric electrolyte plate having anodic material deposited upon a first face thereof facing said first flow channel and cathodic material deposited upon a second face thereof.

3. The oxidation cell of claim 2 wherein said chamber forming means includes a second transparent quartz plate having a first face adjacent a second face of said ultraviolet radiation source and a second face having a second flow channel, said second quartz plate having aqueous solution source inlet means and second outlet means in communication with said second flow channel; wherein said electrolytic cell means comprises a second solid polymeric electrolyte plate having anodic material deposited upon a first face thereof facing said second flow channel and cathode material deposited upon a second face thereof, and including means for providing open communication between first quartz plate outlet means and second quartz plate inlet means.

4. The oxidation cell of claim 2 or 3 wherein hydrogen cavity forming means comprises a hydrogen collection plate member having a hydrogen impervious outer perimeter, and a hydrogen pervious inner portion, a first face of which faces a cathode plate and a second face of which faces a hydrogen impervious cover plate, having hydrogen outlet means.

5. An oxidation cell comprising a vessel having walls, a top and a bottom, an elongated ultraviolet light source extending into said vessel through an opening in said top and being substantially coaxial with said vessel, a solid membrane, comprising a solid polymeric electrolyte open cylinder having anodic material deposited upon the inner wall and having cathodic material deposited upon the outer wall thereof, wherein said membrane cylinder is within said vessel and coaxial therewith, and said membrane is spaced inward of said vessel wall to form a hydrogen cavity; means for sealing said hydrogen cavity; hydrogen outlet means extending from said hydrogen cavity through said vessel wall via an opening provided therein; carbon dioxide sensing means extending into said vessel via an opening provided in said vessel top; mixing means within said vessel; aqueous solution inlet means communicating with the interior of said vessel via an opening in said top; and outlet means for said aqueous solution communicating with the interior of said vessel via an opening in said wall.

6. A system for use in measuring organic carbon in aqueous solution comprising in combination:

(a) means for withdrawing a sample of aqueous solution from a source of said aqueous solution:

(b) means for filtering particulate matter from said sample having an inlet in communication with said sample withdrawing means and having an outlet;

(c) first valve means, having an open and closed position, having an inlet in communication with said filtering means and an outlet;

(d) an oxidation cell for oxidizing organic carbon in said aqueous solution, having an aqueous solution inlet in communication with said first valve outlet, and an aqueous solution outlet, wherein said oxidation cell comprises means for providing a chamber for said aqueous solution sample, an ultraviolet radiation source interior of said chamber, means for detecting carbon dioxide interior of said chamber, means for mixing said aqueous solution interior of said chamber, electrolytic cell means having a solid electrolyte and having an anode in communication with said aqueous solution chamber, and having a cathode remote from said aqueous solution chamber, and means for forming a hydrogen cavity in communication with said cathode and remote from said aqueous solution chamber;

(e) second valve means having an open and closed position, having an inlet in communication with said aqueous solution chamber outlet, and having an outlet; and (f) means for returning aqueous solution from said second valve means outlet to said aqueous solution source.

7. A system for use in determining organic carbon present in an aqueous solution comprising in combination:

(a) sampling means within the system for withdrawing a sample of aqueous solution from a source of aqueous solution;

(b) an electrolysis cell in open communication within the system and selectively energized for electrolysis of water in said aqueous solution sample into oxygen and hydrogen;

(c) ultraviolet radiation means in radioactive communication with that portion of the aqueous solution sample within said electrolysis cell and selectively energized for catalytic reaction of substantially all organic carbon present in the sample to carbon dioxide; and (d) carbon dioxide sensor means in communication with said sampling means for detecting concentration of carbon dioxide in the aqueous solution sample both prior to oxidation and radiation of the sample and subsequent to oxidation and radiation.

* * * * *